United States Patent [19]

Ko et al.

[11] Patent Number: 4,748,117

[45] Date of Patent: May 31, 1988

[54] METHOD FOR FORMING AMPHOTERICIN B CRYSTALS IN FERMENTATION BROTH

[75] Inventors: Raphael Y. Ko, Princeton; Laszlo J. Szarka, East Brunswick, both of N.J.

[73] Assignee: E. R. Squibb & Sons, Inc., Princeton, N.J.

[21] Appl. No.: 852,591

[22] Filed: Apr. 16, 1986

Related U.S. Application Data

[63] Continuation-in-part of Ser. No. 528,384, Sep. 1, 1983, abandoned.

[51] Int. Cl.[4] .................... C12P 19/62; C12R 1/465
[52] U.S. Cl. .................................. 435/76; 435/262; 435/276; 435/886; 514/31
[58] Field of Search ............... 435/122, 886, 262, 128, 435/804, 276, 76, 812; 514/31

[56] References Cited

U.S. PATENT DOCUMENTS

| | | | |
|---|---|---|---|
| 2,908,611 | 10/1959 | Ductcher et al. | 435/76 |
| 2,908,612 | 10/1959 | Ductcher et al. | 435/76 |
| 3,914,409 | 10/1975 | McGahren et al. | 424/119 |
| 4,177,265 | 12/1979 | Michel et al. | 424/119 |

OTHER PUBLICATIONS

Merck Index, #611, (1983), p. 85.

*Primary Examiner*—Charles F. Warren
*Assistant Examiner*—Elizabeth A. Hanley
*Attorney, Agent, or Firm*—Lawrence S. Levinson; Burton Rodney

[57] ABSTRACT

A new method is provided for forming crystals of amphotericin B directly in fermentation broth which crystals are easily separable without use of costly solvent extraction techniques which method includes a direct microbial cell autolysis step to induce crystal formation.

13 Claims, No Drawings

METHOD FOR FORMING AMPHOTERICIN B CRYSTALS IN FERMENTATION BROTH

REFERENCE TO OTHER APPLICATIONS

This application is a continuation-in-part of U.S. application Ser. No. 528,384, filed Sept. 1, 1983 now abandoned.

FIELD OF THE INVENTION

The present invention relates to a method of fermentation especially adapted for use in high yielding amphotericin B fermentation and, more particularly, to a method for forming amphotericin B crystals directly in fermentation broths.

BACKGROUND OF THE INVENTION

Until now, crystals of amphotericin B were prepared from fermentation broth through elaborate recovery procedures which included costly filtration, solvent extraction and crystallization steps.

DESCRIPTION OF THE INVENTION

In accordance with the present invention, crystallization of amphotericin B is induced directly in the fermentation broth which incorporates a water-soluble or water-insoluble fermentation medium, such as described in U.S. Pat. No. 2,908,611, which fermentation medium includes a nitrogen source, a carbon/energy source, and optionally one or more inorganic salts for process control.

In addition, in accordance with the present invention, a process is provided for forming crystals of amphotericin B directly in fermentation broth which process includes providing a fermentation medium as described above, growing *Streptomyces nodosus* in such fermentation medium and inducing crystallization of amphotericin B and microbial cell autolysis. Crystallization and autolysis can be carried out by heating the broth at a sufficient temperature, at least 50° C. and preferably from about 70° C. to about 130° C., for a sufficient period, for example, from about 1 minute to about 10 hours, and preferably from about 10 to about 45 minutes, to induce formation of crystals of amphotericin B.

The crystallization can also be initiated by seeding amphotericin B crystals in the fermentation broth during the fermentation, preferably from about 10 to about 40 hours after start of fermentation.

Autolysis can also be carried out by the use of enzymes, such as lysozyme or other comparable enzyme which has lytic effect on the cell wall.

Where an enzyme or seeding is employed, less heat treatment may be necessary.

The fermentation media employed in the method will contain a nitrogen source in an amount within the range of from about 0.1 to about 20%, and preferably from about 0.5 to about 5% by weight of the media. Examples of suitable nitrogen sources include casein hydrolysate, cottonseed or its derivatives, corn steep liquor, soybean meal or any other comparable organic or inorganic N sources or their soluble derivatives.

The carbohydrate source will be present in the fermentation media in an amount within the range of from about 0.5 to about 20% and preferably from about 0.5 to about 10% by weight. Examples of suitable carbohydrate sources include starch, dextrin, sugars such as maltose, lactose and glucose, glycerol and the like.

The fermentation media employed in the method of the invention may optionally include other conventional fermentation medium components such as one or more inorganic salts which aid in process control. Examples of such inorganic salts include, but are not limited to, $CaCO_3$, $KH_2PO_4$, $(NH_4)_2SO_4$, $MgSO_4$, $MnSO_4$ or $Na_2HPO_4$. The fermentation media may also contain one or more antifoam agents such as silicone antifoam.

A preferred fermentation medium formulation includes from about 1 to about 6% by weight of organic nitrogen source, preferably soy bean meal, from about 2 to about 10% by weight glucose as the carbohydrate source, optionally from about 0.01% to about 0.2% by weight of one or more inorganic salts, preferably calcium carbonate and potassium dihydrogen phosphate, and optionally from about 0.05% to 2% by weight silicone antifoam.

In a preferred embodiment of the method of the invention for forming separable crystals of fermentation product (amphotericin B) in the fermentation broth, the fermentation medium may be completely water-soluble. The fermentation medium is used in the amphotericin fermentation employing the procedure as described in U.S. Pat. No. 2,908,611.

The harvest broth is then heated at a temperature of at least 50° C. for a sufficient length of time, for example, for 10-15 minutes to effect microbial cell autolysis which results in the formation of crystals of amphotericin B. In another embodiment, lysozyme or other proteolytic enzyme (such as proteases, glucanase, papain, trypsin or pepsin) may be added to the fermentation broth, at harvest, at a pH range of 5-7.5, and at a temperature of from about 20° to about 80° C. for from about 30 minutes to about 5 hours. Then, the temperature is raised to 90° C. or higher for 30 minutes to complete the crystal generation.

In another preferred method for carrying out the crystallization, during the fermentation from about 0.01 to about 0.1% w/v sterile amphotericin B crystals (based on volume of broth), can be introduced into the fermentor at 10 to 40 hours of fermentation; thereafter the fermentation is continued as described above, with heating (as described for the autolysis step) or without heating. At the end of the fermentation, amphotericin B microcrystals are present in the fermentation broth which crystals may be separated. The application of the heat is advantageous in addition to the seeding procedure.

The amphotericin crystals are easily separable from the broth by any solid/liquid separation procedure including a flotation technique.

The following Examples represent preferred embodiments of the present invention.

EXAMPLE 1

Crystals of amphotericin B were prepared as described below.

A 20-liter batch of *Streptomyces nodosus* ATCC 14899 was fermented for the production of amphotericin B with the inoculum development and fermentation condition listed below:

Inoculum Development

A. First Stage

Inoculum Source: Frozen vial of culture *Streptomyces nodosus* ATCC 14899
Medium:

| | | |
|---|---|---|
| Glucose | 1% | |
| N-Z Amine B | 1.5% | |
| Yeast Extract | 1.0% | |
| NaCl | 0.5% | |
| CaCO$_3$ | 0.1% | | pH adjusted to 6.8–7.0.
Volume: 100 ml in 500 ml flask.
Sterilization: 30 minutes at 121° C.
Temperature: 25° C.
Incubation: 48 hours on a reciprocating shaker at 220 rpm.

B. Second Stage

Inoculum Source: 10% from first stage.
Medium: Same as first stage.
Sterilization: 30 minutes at 121° C.
Volume: 100 ml in 500 ml flask.
Temperature: 25° C.
Incubation: 48 hours on a reciprocating shaker at 220 rpm.

Germination

Medium:

| | | |
|---|---|---|
| Nutrisoy Flour | 5.0% | |
| Cornsteep Liquor | 1.6% | |
| NaCl | 0.5% | |
| Silicon Antifoam | 0.1% | |

Sterilization: 40 minutes at 121° C.
Temperature: 28° C.
Agitation: 0.7 HP/100 U.S. Gallons.
Aeration: IVVM.
Germination Cycle: 28 hours.
Inoculum Size: 100 ml from the second flask stage.
Fermentation Condition
Medium:

| | | |
|---|---|---|
| Glucose | 7.0% | |
| Soybean Oil Meal | 2.5% | |
| CaCO$_3$ | 0.9% | |
| KH$_2$PO$_4$ | 0.01% | |
| Silicon Antifoam | 0.02% | |

Sterilization: 45 minutes at 121° C.
Temperature: 25° C.
Agitation: 3.5 HP/100 U.S. gallons.
Aeration: 1 VVM.
Fermentation Cycle: 136 hours.
Inoculum Size: 14% from germination stage.
The resulting harvest broth contained 2050 γ/ml of amphotericin B and 390 γ/ml of amphotericin A.

Microscopic examination of the harvest broth did not reveal any crystals in the broth. The broth was heated at 60° C. for 15 minutes. Upon microscopic examination, the broth was found to contain an abundance of crystals of amphotericin B which were easily separable from the harvest broth by flotation or other inexpensive separation techniques.

EXAMPLE 2

Recovery of Amphotericin Powder from Fermentation Broth

The fermentation aspect of the Example was identical to Example 1 except the fermentation medium was filtered to remove undigested soybean residuals using a Sparkler filter lined with cotton fabric. The filtrate obtained was then sterilized again and used as fermentation medium. The resulting harvest broth contained 960 γ/ml of amphotericin B after 112 hours of fermentation. The fermentation broth was then cured at 120° C. for several minutes to induce amphotericin crystal formation. After cooling to room temperature, the amphotericin crystals were then separated by centrifugation and dried at 15 mm Hg 25° C. for 3 hours. Such recovered crystals were found to contain 79 γ amphotericin B/mg of crystals with overall recovery yield of 95%.

EXAMPLE 3

Enzymatic Treatment and Heating

Following the procedure in Example 2, after curing the fermentation broth at 120° C. for several minutes to induce amphotericin B crystallization, the broth was cooled to and maintained at 35° C. and pH around 7.0; then lysozyme was added to the broth and reacted for 2 hours to partially lyse the mycelial cells. Lysozyme was added at a concentration of 4000 *unit/ml of broth. Amphotericin B crystals were then separated from the broth by centrifugation and acetone dried. Such powder was found to contain an even higher amphotericin B content than the product of Example 2.

*One unit is defined as the enzyme activity that will produce a $\Delta A_{450}$ of 0.001 per minute at pH 6.24 at 26° C.

EXAMPLE 4

Seeding

The procedure of Example 2 was followed except that 0.1 g/l of crystals of amphotericin B was added 40 hours after start of fermentation.

At the end of the heating step (after fermentation), crystals of amphotericin B were recovered.

EXAMPLE 5

Formation of Amphotericin B Crystals in Soluble Fermentation Medium

The fermentation aspect of this example was identical to Example 1 except 2.5% soybean oil in the fermentation medium was replaced with 1.25% soluble form of spray dried corn steep liquor (supplied by Roquette Corporation).

The broth was heated at about 75° C. for 15 minutes. After the heat treatment the broth contained amphotericin B crystals and partially lysed mycelium. The crystals of amphotericin B were then separated from the liquid by centrifugation and they were dried at 15 mm Hg at 25° C. for 3 hours. The overall recovery yield of amphotericin was 95%.

What is claimed is:

1. A method for producing crystals of amphotericin B directly in a fermentation medium, which consists essentially of cultivating a strain of *Streptomyces nodosus* in a fermentation medium which is free of organic solvent for amphotericin B until substantial antifungal activity is imparted to said medium, heating the medium to a temperature of from about 70° to about 130° C. for at least 10 minutes to form crystals of amphotericin B, and recovering substantial amounts of said crystals of amphotericin B from said medium.

2. The method for producing crystals of amphotericin B as defined in claim 1 further including the step of adding crystals of amphotericin B to the fermentation medium to induce crystal formation.

3. The method as defined in claim 1 wherein the medium containing the amphotericin B is heated for a period of from about 1 minute to about 10 hours to cause formation of crystals of amphotericin B.

4. The method as defined in claim 3 wherein the fermentation-broth containing the amphotericin B is heated to about 121° C. for about 20 minutes to cause formation of crystals of amphotericin B.

5. The method for producing amphotericin B crystals as defined in claim 1 further includes the step of adding lysozyme, protease, glucanase, papain, trypsin or pepsin after the heating step to complete the crystal formation.

6. The method for producing amphotericin B crystals as defined in claim 5 wherein lysozyme is added.

7. The method as defined in claim 2 wherein crystals of amphotericin B are introduced into the fermentation medium from about 10 to about 40 hours after start of cultivating.

8. The method as defined in claim 7 wherein said amphotericin B crystals are added in an amount of from about 0.01 to about 0.1% weight/volume based on the volume of fermentation medium.

9. The method as defined in claim 1 wherein the fermentation medium is comprised of a nitrogen source in an amount within the range of from about 0.1 to about 20% by weight of the fermentation medium, a carbohydrate source in an amount within the range of from 0.5 to about 20% by weight of the fermentation medium, up to about 0.2% by weight of one or more inorganic salts, and up to about 2% by weight of one or more anti-foam agents.

10. The method as defined in claim 9 wherein the nitrogen source is soybean oil meal or corn steep liquor, and the carbohydrate source is glucose.

11. The method as defined in claim 9 including one or more inorganic salts to aid in process control.

12. The method as defined in claim 10 wherein the inorganic salts are $CaCO_3$ and $KH_2PO_4$.

13. The method as defined in claim 9 including a silicon antifoam agent.

* * * * *